United States Patent [19]

Tanaka et al.

[11] Patent Number: 4,469,946
[45] Date of Patent: Sep. 4, 1984

[54] FLUORESCENT GAS ANALYZER

[75] Inventors: Masaru Tanaka; Naoki Noguchi; Kozo Ishida, all of Kyoto, Japan

[73] Assignee: Horiba, Ltd., Kyoto, Japan

[21] Appl. No.: 366,417

[22] Filed: Apr. 7, 1982

[30] Foreign Application Priority Data

Apr. 24, 1981 [JP] Japan ................................ 56-62723

[51] Int. Cl.³ .............................................. G01J 1/42
[52] U.S. Cl. ..................................... 250/373; 250/343
[58] Field of Search ......................... 250/343, 372, 373

[56] References Cited

U.S. PATENT DOCUMENTS 3,795,812  3/1974  Okabe ................................ 250/373
3,845,309 10/1974  Helm et al. .
4,260,890  4/1981  Wright et al. ...................... 250/373

OTHER PUBLICATIONS

Ashton et al., "The use of double-beam detection systems with pulsed sources of vacuum ultraviolet radiation," Journ. of Phys. E. Scien. Inst. (Gt.B) vol. 3 (Sep. 1970).

Primary Examiner—Janice A. Howell
Attorney, Agent, or Firm—Wenderoth, Lind & Ponack

[57] ABSTRACT

A fluorescent gas analyzer for analyzing gases by the fluorescence method. A flashtube which is operated in its pulse mode is used as a light source. First and second optical detectors respectively detect light of a first and second wavelength range, the light of the first wavelength range being emitted by the light source and the light of the second wavelength range being emitted from a gas sample irradiated by the light source. A pair of integrators respectively integrate the outputs of the first and second detectors. Processing means, including sample and hold circuits and a synchronous detector, are used to further process the signals so that the system output is independent of deterioration of the light source and fluctuations in the strength of the light source output and independent of stray capacitance effects.

7 Claims, 2 Drawing Figures

FLUORESCENT GAS ANALYZER

BACKGROUND OF THE INVENTION

1. Field of the Invention

The present invention relates to a fluorescent gas analyzer for analyzing gases such as $SO_2$ and the like by the fluorescence method; in particular, the present invention relates to a fluorescent gas analyzer which is operated in a pulse mode.

2. Description of the Prior Art

In prior art fluorescent gas analyzers of the pulse mode type, a gas electric discharge flashtube, which is used as a light source, is operated in its pulse mode, and radiant energy of a first wavelength range is applied to a sample placed in a sample chamber. Fluorescent radiant energy of a second wavelength range, which is emitted from the sample due to the application of the radiant energy of the first wavelength range to the sample, is detected by means of an optical detector. The detected electric signals are accumulated in a capacitor during the time period when the flashtube emits the fluorescent energy of the first wavelength range (said time period hereinafter referred to as the period of duration of a flash). The accumulated (i.e.—integrated) voltage of the capacitor is discharged through an electric resistance during the time period when the flashtube has stopped emitting the radiant energy of the first wavelength range (said time period hereinafter referred to as the intervals between flashes). The integrated voltage accumulated in the capacitor is held in a sample and hold circuit as a sample voltage at the time when the flashtube stops emitting the radiant energy of the first wavelength range (said time hereinafter referred to as the flash completion time), and the sample voltage is output through a low-pass filter as a continuous signal which substantially follows the sample voltage. Thus, according to such prior art analyzers, a continuous measurement is possible even when the analyzer is operated in the pulse mode. In addition, the prior art analyzers have an advantage in that an accurate and reliable gas analysis is possible, except for the influence caused by fluctuations in the output of the light source, the deterioration thereof and the like, because the integrated voltage which is accumulated by the capacitor is the voltage value which responds to the radiant energy of the second wavelength range emitted from the sample.

It is, however, inevitable that the light source deteriorates and has fluctuations in its strength when used in a fluorescent gas analyzer of the prior art type. Thus, the fluorescent gas analyzers of the prior art type have a disadvantage in that the fluctuation of the strength of the light source leads to fluctuations in the strength of the fluorescent radiant energy of the second wavelength range emitted from the sample and it thereby appears that the apparent concentration of gas is changed and as a result thereof, errors in the measurement occur. Furthermore, it is feared that the continuous measurement is meaningless in itself because these errors of measurement are apt to be increased in proportion to the progress of the deterioration of the light source during its long term operation.

SUMMARY OF THE INVENTION

It is, therefore, an object of the present invention to provide a fluorescent gas analyzer by which an accurate and reliable gas analysis is possible, regardless of the fluctuations in the output of the light source and the like by preventing the errors of measurement accompanied by the fluctuations of said light source and the like.

DESCRIPTION OF THE PREFERRED EMBODIMENTS

One of the preferred embodiments will be described below by reference to the drawings.

Figure 1:
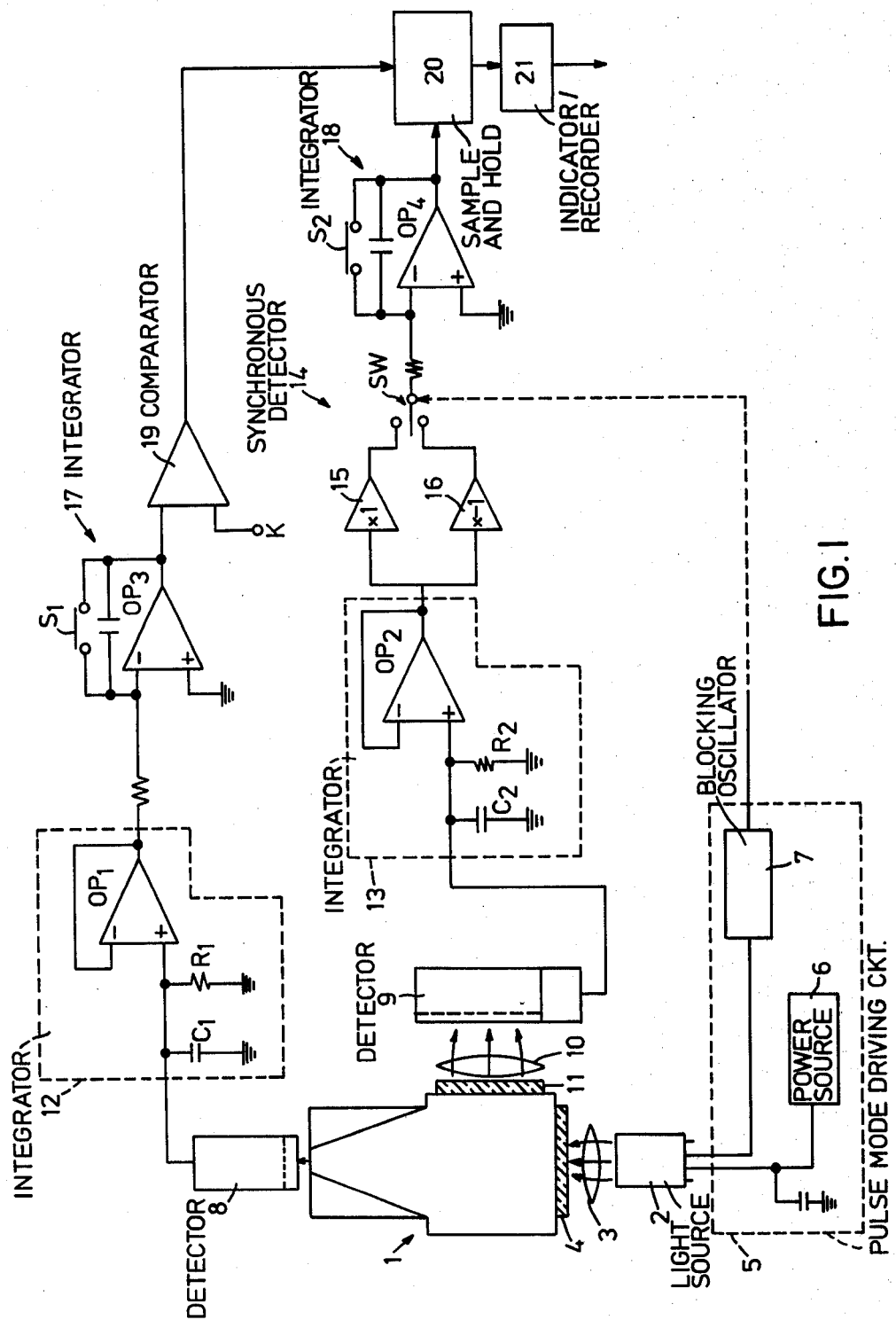
FIG. 1 is a circuit diagram showing one of the preferred embodiments of the present invention.
Figure 2A:
FIGS. 2(a)-2(f) are diagrams showing the waveforms at several points in the circuit shown in FIG. 1.

Referring now to FIG. 1, element 1 is a sample chamber into which a sample, for example, sulfur dioxide gas ($S_{O2}$), is introduced. Element 2 is a light source consisting of, for example, a xenon lamp; the light source 2 is optically connected to the sample chamber 1 through a lens 3 and a filter 4. The filter 4 is an ultraviolet band-pass filter, which has a bandwidth of about 200 Å and a wavelength of about 2,200 Å as the center wavelength thereof. Accordingly, the sample placed in the sample chamber 1 is irradiated by radiant energy of a first wavelength range defined by the filter 4. Element 5 is a pulse mode driving circuit, which is driven in the pulse mode, for controlling the light source 2 so as to generate repeated flashes. The pulse mode driving circuit 5 consists of a power source 6 and a blocking oscillator 7. The blocking oscillator 7 generates, for example, positive blocking wave pulses having a period of duration of about 100 microseconds at intervals of 5 milliseconds (refer to FIG. 2(a)). Element 8 is a first optical detector which is arranged on the same axis as the light source 2 and optically connected to the light source 2 through the sample chamber 1. The radiant energy of the first wavelength range, which passed through the filter 4, is incident upon the detector 8. A vacuum photodiode is used for the optical detector 8 because such radiant energy is comparatively strong. Element 9 is a second optical detector which is arranged on an axis perpendicular to the axis connecting the light source 2 to the first optical detector 8 and is optically connected to the sample chamber 1 through a lens 10 and a filter 11. The filter 11 selectively passes the radiant energy of such a wavelength range characteristic of the fluorescence emitted from the sample to be measured. In the case of the embodiment shown in FIG. 1, a filter having a bandwidth of about 1,000 Å and a wavelength of about 3,600 Å as the center wavelength thereof, is used because $SO_2$ gas is being used as the sample. The fluorescent radiant energy of the second wavelength range, which is emitted from the sample and defined by the filter 11, is incident upon the second optical detector 9. A photomultiplier tube is used for the second optical detector 9 because the fluorescent radiant energy of the second wavelength range is less than the radiant energy of the first wavelength range.

Figure 2B:
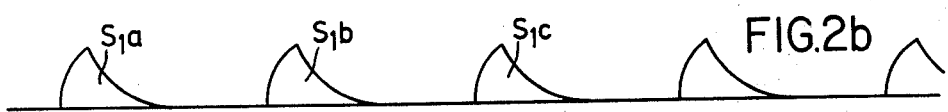

Element 12 is a first circuit means for integrating electric signals which are output from the first optical detector 8. The signals are integrated during the time period of the duration of each flash. The integrated voltage is discharged during the time period when the flashtube has stopped emitting raidant energy of the first wavelength range. Element 13 is a second circuit means for integrating electric signals which are emitted from the second optical detector 9. The signals are integrated during the period of the duration of each flash and the integrated voltage is discharged during the intervals between flashes. The circuit means 12 and 13 consist or RC charging/discharging circuits $C_1$, $R_1$, $C_2$, $R_2$ and operational amplifiers $OP_1$ and $OP_2$ which are used for amplifying the voltage generated by the RC charging/discharging circuits $C_1$, $R_1$, $C_2$, $R_2$. It is desirable that capacitors and resistances of the same values be used in both circuit means 12 and 13. In addition, it is desirable that the time constant be selected so that the charge, which was accumulated in the capacitor, may be almost completely discharged during the intervals between flashes (4.9 milliseconds). FIG. 2(b) shows a voltage signal obtained from the first circuit means 12 and FIG. 2(c) shows a voltage signal obtained from the second circuit means 13.

Figure 2C:
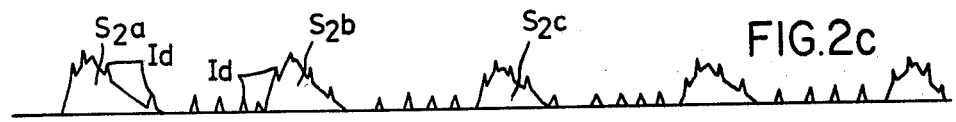
Figure 2D:
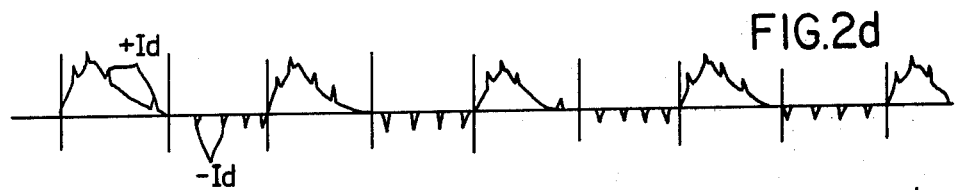

Element 14 is a synchronous detector circuit consisting of: a non-inverting amplifier 15 for outputting the electric signals obtained from the second circuit means 13, and an inverting amplifier 16 for outputting an inverted version of the electric signals from circuit means 13, and a synchronous switch SW for alternatively switching between the non-inverted amplifier 15 output and the inverted amplifier 16 output at a definite rate. In the preferred embodiment shown in FIG. 1, the switch SW is constructed so that it may be synchronized with the blocking oscillator 7 so as to be switched during each half cycle of the oscillating frequency of the blocking oscillator 7. Accordingly, as shown in FIG. 2(d), the electric signals output from the second circuit means 13 are output unchanged during the half cycle in which flashes are generated, and the electric signals output from the second circuit means 13 are inverted during the following half cycle. The following is the reason why the electric signals are inverted during every other half cycle:

The dark current (Id shown in FIG. 2(c)), which is emitted from the second optical detector 9, cannot be disregarded in the case when fluorescent radiant energy, which is detected by the second optical detector 9, is weak. However, the dark current is always continuously generated during either the period of duration of the flash or the intervals between flashes and only the dark current can thereby be compensated by inverting phases during every other half cycle in the following integration step. Furthermore, the changing-over of the switch SW is not limited to every other half cycle. The changing-over action of the switch SW may be carried out so that the electric signals may be output by the non-inverting amplifier 15 for the ¼ cycle in which the flashes are generated, and the electric signals may be output by the inverting amplifier 16 for the ¼ cycle directly before the generation of flash. In addition, the synchronous detector circuit 14 is not arranged after the first circuit means 12 because radiant energy of the first wavelength range is sufficiently strong in comparison with the dark current and the dark current component can therefore be disregarded. However, a similar detector circuit may be also arranged after the first circuit means 12 if needed.

Figure 2E:
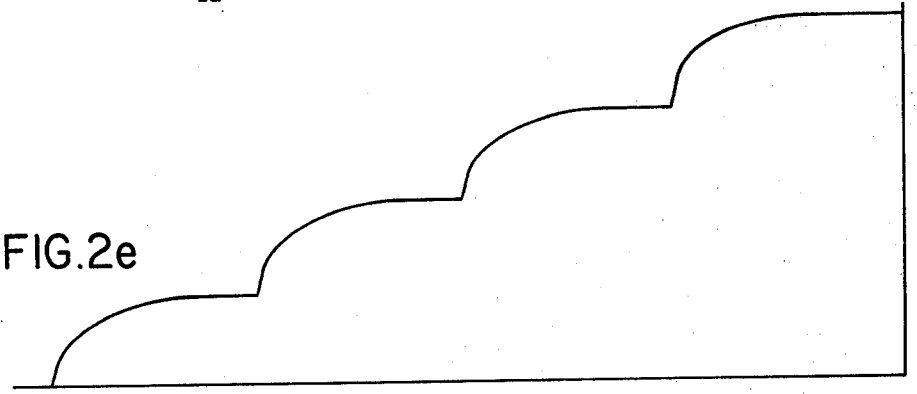
Figure 2F:
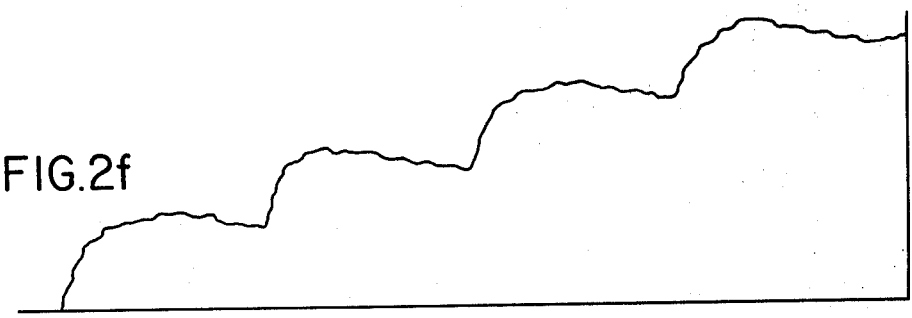

Element 17 is an integrator for integrating the electric signals obtained from the first circuit means 12. Element 18 is an integrator for integrating the electric signals obtained from the synchronous detector circuit 14. Integrators 17 and 18 respectively include operational amplifiers $OP_3$ and $OP_4$ as the main component thereof. FIGS. 2(e) and 2(f) respectively show the output of the integrators 17 and 18. It is found from FIGS. 2(e) and 2(f) that integrators 17 and 18 respectively integrate the areas $S_{1a}$, $S_{1b}$- - -, $S_{2a}$, $S_{2b}$- - -which are formed under the charging/discharging output curves obtained from the first circuit means 12 and the second circuit means 13. Such a configuration, in which the areas $S_{1a}$- - -, $S_{2a}$- - -are integrated, has an advantage in that the errors caused by stray capacity and the like in the first circuit means 12 and the second circuit means 13 can be prevented. That is to say, although the value having the same physical meaning as the value obtained by integrating the areas, as described above, can be obtained also by integrating (substantially adding) the peak values output from the first circuit means 12 and the second circuit means 13 at the flash completion time, the peak values are dependent upon the capacitances of capacitors $C_1$ and $C_2$ and the peak values are thereby dependent upon the stray capacity of the circuit connected to these capacitors and essentially parallel to these capacitors. Such influences are presented in the form of measurement errors because stray capacity fluctuates in dependence upon temperature, vibration and the like. Accordingly, in the prior art method, in which the peak values are integrated, although it is necessary to increase the capacitance of the capacitors $C_1$ and $C_2$ in order to decrease the influence of stray capacity as far as possible, the increase of the capacity leads conversely to a decrease of the peak values and the S/N ratio is thereby deteriorated. On the contrary, according to the above described method according to the present invention in which the areas $S_1$ and $S_2$ are integrated, stable electric signals can be obtained regardless of stray capacity and an accurate measurement is thereby possible because the areas are functions of electric resistances $R_1$ and $R_2$ used for electric discharge. Element 19 is a comparator for comparing the value of the integration output obtained from the integrator 17 with a predetermined value K and for emitting an agreement signal when the value of the integration output obtained from the integrator 17 becomes equal to the predetermined value K. Element 20 is a sample and hold circuit for sampling and holding the value of the integration of voltage signals, which were integrated by the integrator 18 at the time when said agreement signal was output the held value corresponding to the second wavelength range. Although the predetermined value K may be arbitrarily selected, the compensating accuracy for compensating for errors of measurement due to the deterioration or fluctuation of the light source 2 is directly proportional to the value of K. That is, high values of K result in high system accuracy. It is, however, desirable that the value K be not so large as to preclude the possibility of a continuous measurement. In general, it is preferable that radiant energy output of the first wavelength range after 100 or more flashes of the light source 2 be almost the same as the value obtained from the first circuit means 12 and the integrator 17. Element 21 is an indicating/recording member such as a meter or the like for indicating and recording the voltage signals obtained from the sample and hold circuit 20.

In the above described configuration, the integration of the voltage signals corresponding to the fluorescent radiant energy of the second wavelength range is also continued until the value of the integration of voltage signals corresponding to radiant energy of the first wavelength range reaches the predetermined value K, even though the light source 2 has deteriorated or fluctuates in its strength. Accordingly, the value of the integration of voltage signals corresponding to the second wavelength range is a value which is dependent only upon the concentration of sulfur dioxide gas contained in the sample and the value is unaffected by the deterioration or fluctuations of the light source 2 in its strength. This is due to the fact that at the time when the value of the integration of the voltage signals corresponding to said first wavelength range reaches the predetermined value K, the deterioration and fluctuations of the light source in its strength have a similar influence upon both the radiant energy in the first wavelength range and the fluorescent radiant energy in the second wavelength range.

In addition, after the comparator 19 has output an agreement signal and after the value of the integration signals which have been integrated in the integrator 18 were output to the sample and hold circuit 20, it is necessary to reset the values of the integration signals held in integrators 17 and 18 in order to obtain the following integration value. In this preferred embodiment, integrators 17 and 18 are provided with reset switches $S_1$ and $S_2$ for resetting. These reset switches $S_1$ and $S_2$ may be adjusted so as to switch on a preset time after the comparator 19 has output the agreement signal.

A fluorescent gas analyzer of the present invention has an outstanding advantage in that the selected gaseous component contained within the sample, such as sulfur dioxide gas ($SO_2$), can be accurately and reliably determined without being influenced by the deterioration and fluctuations of the strength of its light source. Furthermore, a fluorescent gas analyzer of the present invention has an additional advantage in that the influences caused by stray capacity in the circuits can be effectively prevented in contradistinction to the prior art method using the peak values because of the fact that the method of the present invention, in which the first circuit means and the second circuit means integrate voltage signals during the period of the duration of the flash and discharge these voltage signals during the intervals between flashes, repeatedly integrate the voltage signals; that is, the integrations are substantially repeated so as to eliminate the effect of stray capacitance.

What is claimed is:

1. A fluorescent gas analyzer for measuring the concentration of fluorescent components contained in a gaseous sample, said analyzer comprising:
    a sample chamber for holding said gaseous sample;
    a light source which is optically connected to said sample chamber for applying radiant energy of a first wavelength range to said sample held within said sample chamber;
    a pulse mode driving circuit operatively electrically connected to said light source for causing said light source to repeatedly generate light flashes;
    a first optical detector for detecting radiant energy of said first wavelength range emitted from said light source and passing through said sample and for generating electric signals corresponding to said detected radiant energy;
    a second optical detector for detecting fluorescent radiant energy of a second wavelength range emitted from said sample placed in said sample chamber and for generating an electric signal corresponding to said fluorescent detected radiant energy;
    a first circuit means operatively electrically connected to said first optical detector and including a first integrator for integrating electric signals which are output from said first optical detector during the duration of each flash of said light source and for discharging a voltage corresponding to said integrated electrical signals from said first optical detector during the intervals between the flashes of said light source and a second integrator operatively connected to said first integrator for continuously integrating an output thereof and including a comparator means for comparing an output of said second integrator with a predetermined value and producing an output signal representative of said comparison;
    a second circuit means operatively electrically connected to said second optical detector and including a third integrator for integrating electric signals which are output from said second optical detector during the duration of each flash of said light source and for discharging a voltage corresponding to said integrated electric signals from said second optical detector during said intervals between the flashes of said light source and a fourth integrator operatively connected to said third integrator for continuously integrating an output thereof;
    a sample and hold circuit for integrating separately and repeatedly voltage signals which are output from said second circuit means by each flash of said light source, and for sampling and holding the value of the integration of voltage signals corresponding to said second wavelength range in response to said comparator means output signal when the value of the integration of voltage signals corresponding to the first wavelength range reaches said predetermined value;
    and an indicating and/or recording means for indicating and/or recording said value output by said sample and hold circuit.

2. A fluorescent gas analyzer as set forth in claim 1, further comprising a synchronous detector circuit which is arranged after said third integrator for outputting voltage signals which are output from said third integrator unchanged during the duration of an electric signal which is generated in response to the flash of said light source and for outputting voltage signals which are inverted versions of the voltage signals output from said third integrator during the intervals between said electric signals.

3. A fluorescent gas analyzer as set forth in claim 2, wherein said synchronous detector circuit comprises: a non-inverting amplifier, an inverting amplifier, and a synchronous switch for alternatively switching-over between the outputs of said non-inverting amplifier and said inverting amplifier at a predetermined rate, said synchronous switch being synchronized with signals from said driving circuit which are used for causing said light source to repeatedly generate flashes.

4. A fluorescent gas analyzer as set forth in claim 1, wherein said predetermined value is selected to be almost equal to the value of the repeated integration of voltage signals output from said first circuit means after said light source has flashed at least 100 times.

5. A fluorescent gas analyzer as set forth in any one of claims 1 to 4, wherein said second optical detector is arranged on an axis which is perpendicular to an axis connecting said light source with said first optical detector.

6. A fluorescent gas analyzer as set forth in any one of claims 1 to 4, wherein a vacuum photodiode comprises said first optical detector and a photomultiplier tube comprises said second optical detector.

7. A fluorescent gas analyzer as set forth in claim 5, wherein a vacuum photodiode comprises said first optical detector and a photomultiplier tube comprises said second optical detector.

* * * * *